United States Patent
Helal et al.

(10) Patent No.: US 7,397,346 B2
(45) Date of Patent: Jul. 8, 2008

(54) DAILY TASK AND MEMORY ASSISTANCE USING A MOBILE DEVICE

(75) Inventors: Abdelsalam A. Helal, Gainesville, FL (US); Carlos M. Giraldo, Gainesville, FL (US); William C. Mann, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 267 days.

(21) Appl. No.: 10/889,147

(22) Filed: Jul. 12, 2004

(65) Prior Publication Data

US 2005/0057357 A1 Mar. 17, 2005

Related U.S. Application Data

(60) Provisional application No. 60/486,018, filed on Jul. 10, 2003, provisional application No. 60/490,717, filed on Jul. 29, 2003.

(51) Int. Cl.
*G08B 1/00* (2006.01)

(52) U.S. Cl. .................. 340/309.15; 340/309.4; 340/309.7; 340/539.11; 340/539.12; 340/573.1; 340/457; 340/691.3; 700/231; 700/233

(58) Field of Classification Search .......... 340/691.3, 340/457, 573.1, 573.4, 539.1, 539.11, 539.12, 340/539.13, 825.36, 825.49, 539.14, 539.19, 340/309.4, 309.15, 309.7; 600/300, 301; 705/2, 3; 30/307.7; 700/231, 233
See application file for complete search history.

(56) References Cited

U.S. PATENT DOCUMENTS

| | | | |
|---|---|---|---|
| 4,803,625 A * | 2/1989 | Fu et al. ............... | 600/483 |
| 5,612,869 A * | 3/1997 | Letzt et al. ............ | 705/3 |
| 5,722,418 A * | 3/1998 | Bro ...................... | 600/545 |
| 5,812,865 A * | 9/1998 | Theimer et al. ....... | 709/228 |
| 5,833,603 A | 11/1998 | Kovacs et al. | |
| 5,872,834 A | 2/1999 | Teitelbaum | |
| 5,961,446 A * | 10/1999 | Beller et al. .......... | 600/300 |
| 6,204,763 B1 | 3/2001 | Sone | |
| 6,362,778 B2 | 3/2002 | Neher | |
| 6,380,858 B1 | 4/2002 | Yarin et al. | |
| 6,404,880 B1 | 6/2002 | Stevens | |
| 6,428,475 B1 | 8/2002 | Shen | |
| 6,453,027 B1 | 9/2002 | Kang et al. | |
| 6,496,111 B1 | 12/2002 | Hosack | |
| 6,553,262 B1 | 4/2003 | Lang et al. | |
| 6,567,672 B1 | 5/2003 | Park et al. | |

(Continued)

OTHER PUBLICATIONS

Mann, W., et al., "Smart Phones for the Elders: Boosting the Intelligence of Smart Homes", Am. Assoc. for Artifical Intell. (AAAI), (Jul. 2002).

(Continued)

*Primary Examiner*—Hung Nguyen
(74) *Attorney, Agent, or Firm*—Akerman Senterfitt

(57) ABSTRACT

A method of task and memory assistance using a mobile communication device can include storing a profile of a user and determining a task to be performed by the user based on the user profile. The method can also include notifying the mobile communication device of the task. The method can further include providing sensory indicators in an increasing order of intervention until an acknowledgement is received from user, or for a predetermined number of notifications.

18 Claims, 5 Drawing Sheets

U.S. PATENT DOCUMENTS

| | | | |
|---|---|---|---|
| 6,678,516 B2 | 1/2004 | Nordman et al. | |
| 6,696,924 B1* | 2/2004 | Socinski | 700/213 |
| 6,774,795 B2 | 8/2004 | Eshelman et al. | |
| 6,961,285 B2* | 11/2005 | Niemiec et al. | 368/10 |
| 2001/0009398 A1* | 7/2001 | Sekura et al. | |
| 2001/0046862 A1 | 11/2001 | Coppinger et al. | |
| 2002/0060243 A1 | 5/2002 | Janiak et al. | |
| 2002/0080034 A1* | 6/2002 | Yahalom et al. | |
| 2002/0116541 A1* | 8/2002 | Parker et al. | |
| 2002/0127145 A1 | 9/2002 | Der Ghazarian et al. | |
| 2002/0128864 A1 | 9/2002 | Maus et al. | |
| 2002/0188467 A1* | 12/2002 | Eke et al. | |
| 2003/0009088 A1 | 1/2003 | Korth et al. | |
| 2003/0013507 A1 | 1/2003 | Sato | |
| 2003/0064732 A1 | 4/2003 | McDowell et al. | |
| 2003/0064749 A1 | 4/2003 | Soini et al. | |
| 2003/0083020 A1 | 5/2003 | Langford | |
| 2003/0087628 A1 | 5/2003 | Michibata | |
| 2003/0208382 A1* | 11/2003 | Westfall et al. | |
| 2003/0212579 A1* | 11/2003 | Brown et al. | |
| 2004/0249250 A1* | 12/2004 | McGee et al. | |
| 2007/0021979 A1* | 1/2007 | Cosentino et al. | |

OTHER PUBLICATIONS

Haigh, K., et al., "The Role of Intelligent Technology in Elder Care", AAAI-02 WS on Automation as Caregiver, (Jul. 2002).

Giraldo, C., "mPCA-A Mobile Patient Care-Giving Assistant for Alzheimer Patients", UbiCog '02, (Sep. 29, 2002).

Helal, S., et al., "Smart Phone Based Cognitive Assistant", UbiHealth, (Oct. 12-15, 2003).

Long, M., "A New Reference Design for Jumpstarting Smartphone Development", E-inSITE, (Feb. 13, 2003).

"Home Automation Systems", National Security, Inc., Internet, viewed (Jun. 3, 2003).

"SmartPhones", Motorola, Internet, (viewed Jun. 3, 2003).

"An Executive White Paper—Secure Mobile Banking Architecture", Consumer Direct Link, Inc., (Sep. 2001).

* cited by examiner

FIG. 6

DAILY TASK AND MEMORY ASSISTANCE USING A MOBILE DEVICE

CROSS-REFERENCE TO RELATED APPLICATIONS

This application claims the benefit of U.S. Provisional Application No. 60/486,018, filed in the United States Patent and Trademark Office on Jul. 10, 2003, and U.S. Provisional Application No. 60/490,717, filed in the United States Patent and Trademark Office on Jul. 29, 2003, the entirety of both which are incorporated herein by reference.

BACKGROUND

1. Field of the Invention

The present invention relates to the field of portable computing devices and, more particularly, to a portable computing device for providing daily task and memory assistance.

2. Description of the Related Art

Persons suffering from cognitive impairments, such as the elderly, often experience memory lapses and other challenges. Such handicaps can cause an elderly person to forget to perform critical daily tasks, such as eating three meals a day, feeding a pet, or taking medication. Further, cognitive impairments can cause an elderly individual to forget how to perform the sequential steps involved in a daily routine, such as getting dressed, or operating a VCR. Moreover, once an elder remembers, or has been reminded, to perform a specific task, the elder may require further assistance locating an object or entity integral to the task, such as a medicine bottle, a phone number, a pet, or the like.

At present, devices designed to assist persons suffering from cognitive challenges have many limitations. For example, mechanisms which are intended to remind an elder to perform a specific task, such as audible and visual indicators, alone often do not sufficiently capture the elder's attention. For instance, many elders also suffer from hearing loss, and may be unable to hear an audible sound, such as a buzzer, alarm, or a recorded voice message. Moreover, even if the elder is capable of hearing an audible reminder, he or she may not remember what the sound represents due to cognitive impairments. Similarly, text messages alone can be problematic if the elder suffers from failing sight, reading challenges, or is unable to locate glasses.

Another limitation of commonly used assistance devices is that they are not portable, and are therefore only operable at a relatively fixed location. Thus, oftentimes the user must be in close proximity to the device in order for it to capture the user's attention. Additionally, such devices do not typically contain an acknowledgement feature which can alert a third party, such as a relative or caregiver, if the user fails to perform the task after being reminded.

What is needed is a memory assistance device for cognitively impaired individuals, such as the elderly.

SUMMARY OF THE INVENTION

The present invention provides a method, a system, and an apparatus for providing remote task and memory assistance within a defined smart space using a mobile communication device (MCD), such as a mobile telephone. More specifically, an MCD can attempt to capture the attention of a user, such as a person suffering from cognitive impairments, by emitting a combination of sensory indicators in an increasing order of intervention and interactivity. Once the user's attention has been successfully captured, the user can be reminded of a critical task to be performed by viewing a video clip describing the task on a local video monitor. Additionally, the system can determine tasks to be performed at a given location within the smart space. When the system determines that the user has arrived at a given location, the MCD can prompt the user to select from the list of tasks associated with the location. Accordingly, step by step instructions on how to perform the task selected by the user can be displayed on a local video monitor.

One aspect of the present invention can include a method of task and memory assistance using a mobile communication device. The method can include storing a profile of a user, determining a task to be performed by the user based on the user profile, and notifying the mobile communication device of the task. The method also can include providing sensory indicators in an increasing order of intervention until an acknowledgement is received from the user, or for a predetermined number of notifications.

In one embodiment, the notifying step can include notifying the mobile communication device over a short range wireless network. The providing step can include emitting audio indicators, emitting vibratory indicators, and emitting olfactory indicators. The method also can include notifying a designated third party if no acknowledgement is detected from the user.

The method also can include determining a location of the mobile communication device. One of a plurality of monitors disposed throughout a defined space can be selected according to the location. The selected monitor can be the monitor that is most proximate to the mobile communication device. Information pertaining to the task can be presented on the selected monitor.

Another aspect of the present invention can include a method for providing task instruction using a mobile communication device. The method can include storing a profile of user tasks, wherein each task is associated with a location within a defined space, determining a location of the mobile communication device within the defined space, identifying one or more tasks associated with the location, and providing a listing of the one or more tasks associated with the location to the user via the mobile communication device.

The method can include selecting one of a plurality of monitors disposed throughout the defined space according to the location, wherein the selected monitor is most proximate to the mobile communication device. Information pertaining to a task selected by the user can be presented upon the selected monitor.

Another aspect of the present invention can include a system for providing memory assistance. The system can include a location tracking mechanism, a mobile communication device configured to interact with the location tracking mechanism, a server in communication with the location tracking mechanism and the mobile communication device, wherein the server is local to the mobile communication device. The server can include a listing of tasks. The system also can include a plurality of monitors. The server can be configured to select one of the plurality of monitors most proximate to the user based upon information from the location tracking mechanism and cause information corresponding to one of the tasks to be presented upon the selected monitor. In one embodiment, the server can deliver video to the selected monitor. The video can specify a sequential set of steps involved in the performance of at least one of the tasks.

Other embodiments of the present invention can include a machine readable storage for causing a machine to perform the steps described herein.

BRIEF DESCRIPTION OF THE DRAWINGS

There are shown in the drawings, embodiments that are presently preferred; it being understood, however, that the invention is not limited to the precise arrangements and instrumentalities shown.

FIG. 6 is a schematic diagram illustrating one embodiment of a graphical user interface (GUI) in accordance with the inventive arrangements disclosed herein.

DETAILED DESCRIPTION OF THE INVENTION

Figure 1:
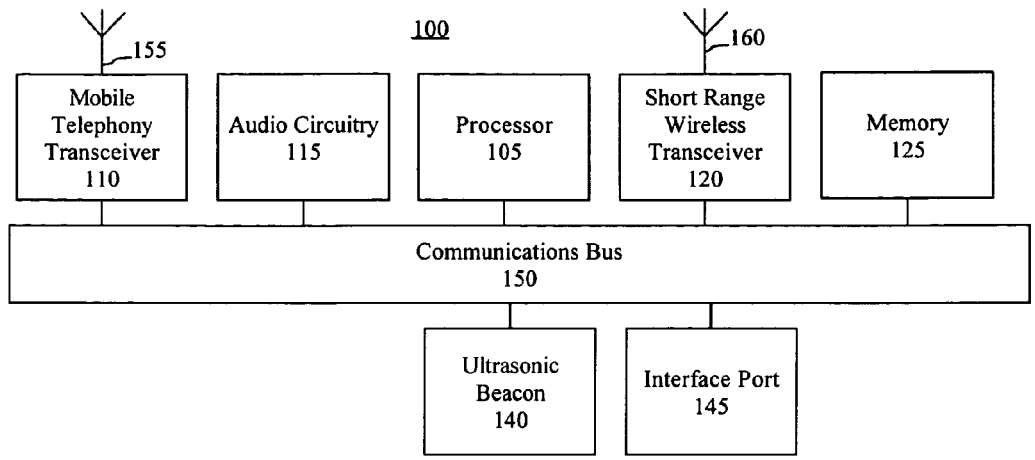
FIG. 1 is a schematic diagram illustrating an embodiment of a mobile communication device (MCD) configured in accordance with the inventive arrangements disclosed herein.

FIG. 1 is a schematic diagram illustrating an embodiment of a mobile communication device (MCD) 100 configured in accordance with the inventive arrangements disclosed herein. As shown, the MCD 100 can include a processor 105, a mobile telephony transceiver 110, audio circuitry 115, a short range wireless transceiver 120, and a memory 125. Each of the aforementioned components can be communicatively linked via a suitable communications bus 150 or other suitable circuitry. For example, the MCD 100 can be implemented as a mobile phone having the features described herein.

The processor 105 can execute a suitable operating system and one or more applications for controlling the various functions of the MCD 100. For example, the processor 105 can execute an operating system that can support the execution of one or more applications intended to run on that platform and which support operation of the various functions and features disclosed herein. As the MCD 100 can include one or more sensors to be described in greater detail herein, the operating system and computing architecture can be designed to support the operation of such sensors. According to one embodiment, the MCD 100 can be compatible with the JAVA 2 Platform, Micro Edition (J2ME®).

The memory 125 can be implemented as random access memory, read-only memory, erasable programmable read-only memory, or any other type of physical memory suitable for use within a mobile communication device, such as the MCD 100. It should be appreciated that the memory 125, while illustrated as a separate component, can be incorporated into the processor 105 or another component. In any case, the memory 125 can include programmatic instructions to be executed by the processor 105 as well as any operational data necessary for operation of the MCD 100.

Wireless signals can be received and sent via the antenna 155 which can be suited for longer-range communications such as conventional cellular or personal communication service (PCS) communications. Accordingly, the antenna 155 can be operatively connected to the mobile telephony transceiver 110. Signals detected by antenna 155 can be provided to the mobile telephony transceiver 110 for processing and decoding. For example, the mobile telephony transceiver 110 can include a codec for coding and decoding information received or to be sent via wireless transmission. The transceiver 110 can make the decoded signals and/or information available to other components of the MCD 100 for processing. Outbound information received by the mobile telephony transceiver 110 can be coded and/or formatted for wireless transmission by the codec and then provided to the antenna 155 for transmission.

Thus, it should be appreciated that the MCD 100 can communicate via conventional cellular telephone and/or PCS telephone calls and access wireless networks, for example using Wireless Access Protocol or another suitable wireless communications protocol, such that the MCD 100 can access the Internet, the Web, and/or a wide area network, as well as any applications and/or services disposed on such networks via a wireless communications link.

The audio circuitry 115 can include a microphone or other audio input transducer for receiving sound and one or more analog-to-digital converters for digitizing the received sound. The audio circuitry 115 further can include one or more digital-to-analog converters for converting digital information into an analog signal. The audio circuitry 115 can include a speaker or other audio output transducer for generating sound from an analog signal as well as one or more amplifiers for driving the speaker.

It should be appreciated that the audio circuitry 115 can include additional processors, such as digital signal processors (DSPs) as may be required for processing audio and performing functions such as audio encoding, audio decoding, noise reduction, and the like. According to one embodiment of the present invention, the audio circuitry can be implemented using one or more discrete components. In another arrangement, the audio circuitry 115 can be implemented using one or more integrated circuits configured to perform the various functions disclosed herein. Thus, the MCD 100 can be configured to play various audio formats from streaming formats to MP3's, or other audio file formats such as .wav or aiff files.

The audio circuitry 115 can also include and/or be communicatively linked to automatic speech recognition (ASR) and synthetic speech generation components that can be used to perform text-to-speech and speech-to-text conversions. When the audio circuitry 115 includes ASR and/or speech generation components, suitable software and/or firmware can be embedded within the audio circuitry 115. When the audio circuitry 115 is communicatively linked to remotely located ASR and/or speech generation components, communications between the audio circuitry 115 and the remotely located components can occur using the mobile telephony transceiver 110, the short range wireless transceiver 120, the interface port 145, or any other suitable elements.

The MCD 100 also can include a short range wireless transceiver 120 as well as an antenna 160 operatively connected thereto. The short-range wireless transceiver 120 can both send and receive data. For example, according to one embodiment of the present invention, the short range wireless transceiver 120 can be implemented as a BlueTooth-enabled wireless transceiver, or as a transceiver configured to communicate via one of the 802.11 family of short range wireless communications specifications. The short range wireless transceiver 120 and accompanying antenna 160 can be configured to communicate using any of a variety of short range, wireless communications protocols and/or systems. Through the short range wireless transceiver 120, the MCD 100 can communicate with a local area network or other short range wireless network. Still, the various examples disclosed herein have been provided for purposes of illustration only and should not be construed as limitations of the present invention.

The MCD 100 further can include an ultrasonic beacon 140. The ultrasonic beacon 140 or transponder can be detected by one or more ultrasonic receivers referred to as pilots or monitors. The pilot devices can be dispersed throughout a room or other environment, known as a "smart" environment, to detect the location of the MCD 100, or any other device having one or more such ultrasonic beacons 140.

It should be appreciated, however, that the present invention is not limited to the use of ultrasonic beacons as a means of determining location. Rather, any suitable technology can be used. For example, the MCD 100 can be equipped with a Global Positioning System receiver or other satellite-based location detection system. In another example, the MCD 100 can include a radio-frequency-based location detection system such as one utilizing radio-frequency identifier tags or another radio-frequency beacon.

The MCD 100 can also include one or more interface ports 145 used to physically connect devices and/or peripherals to the MCD 100. For example, the interface port 145 can be a standard wall jack to initiate telephone calls over the Public Switched Telephone Network (PSTN). The interface port 145 can also include a universal serial bus (USB) port, a firewire (IEEE 1394) port, a parallel port, a COM port like an RS-232 port, an Ethernet port, an audio port, or the like. Use of the interface port 145 for communicatively linking the MCD 100 with external devices can be advantageous in situations where wireless connectivity may not be available, is intermittent, or otherwise unsuitable for a particular purpose.

Each of the various components of the MCD 100 disclosed herein can be communicatively linked with one another using appropriate circuitry, whether through the memory 125, one or more additional memories (not shown), the processor 105, one or more additional interface processors or logic controllers (not shown), and/or the communications bus 150. One skilled in the art will recognize that the components disclosed herein can be embodied in other forms and that the configuration disclosed and described with reference to FIG. 1 is provided for purposes of illustration only. For example, the components can be implemented as one or more discrete components, as one or more processors, logic controllers, DSPs, or any combination thereof.

Figure 2:
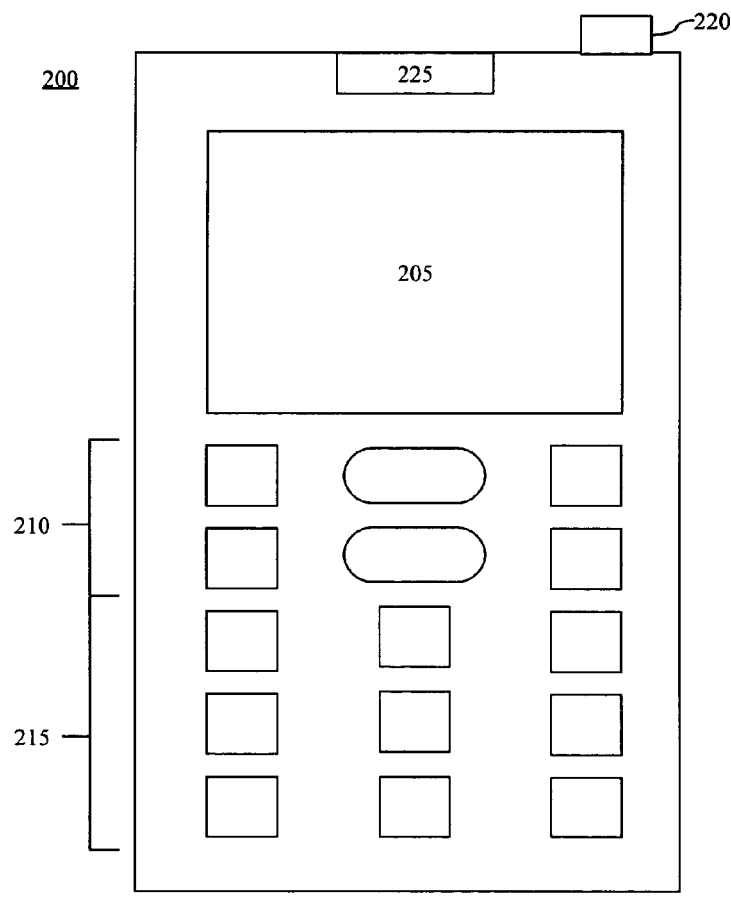
FIG. 2 is a schematic diagram illustrating an embodiment of an MCD in accordance with the inventive arrangements disclosed herein.

FIG. 2 is a schematic diagram illustrating an embodiment of an MCD 200 in accordance with the inventive arrangements disclosed herein. As shown, the MCD 200 can include a presentation element 205, one or more control or operational keys 210, which can include special function command keys for operation of one or more of the functions disclosed herein, alphanumeric keys or buttons 215, and an antenna 220 (which may be configured to be fully located within the MCD 200). The MCD 200 further can include a battery or other power source (not shown). Notably, the MCD 200 can include a rechargeable battery as well as additional power sources to enable the MCD 200 to be active for extended periods of time.

The physical arrangement of the MCD 200 has been provided for purposes of illustration only. As such, it should be appreciated that the various components can be located in any of a variety of different configurations. For example, the MCD 200 can include additional keys or controls disposed on the frontal portion or the sides of the unit.

According to one embodiment of the present invention, the physical arrangement of the MCD 200 can be conducive for use by visually impaired individuals or those that may have difficulty accessing and/or operating the keys and/or controls of conventional mobile computing devices, such as the elderly, persons with physical disabilities, or other infirmities. For example, the control keys 210 and the alphanumeric keys 215 of the MCD 200 can be larger in size than conventional mobile device keys and can be spaced a greater distance from one another with respect to both the width and length of the MCD 200. That is, the horizontal key spacing and the vertical key spacing can be greater than that found with conventional mobile devices. Further, the control keys 210 can include Braille markings for key identification purposes.

The MCD 200 can include a visual display 205, such as a liquid crystal display (LCD) implemented in either grayscale or color, a touch screen, or any other type of suitable display screen. The display screen 205 can be larger than those found on conventional mobile computing devices and can have an increased contrast ratio if so desired.

As noted, the MCD 200 can include a variety of sensors. As shown in FIG. 2, the MCD 200 can be configured with one or more location detection mechanisms 225. While the location detection mechanism 225 can be positioned on the MCD 200 in any of a variety of different locations, according to one embodiment, the location detection mechanism 225 can be positioned at the top portion of the MCD 200. Other sensors can be located throughout the exterior portion of the MCD 200.

Figure 3:
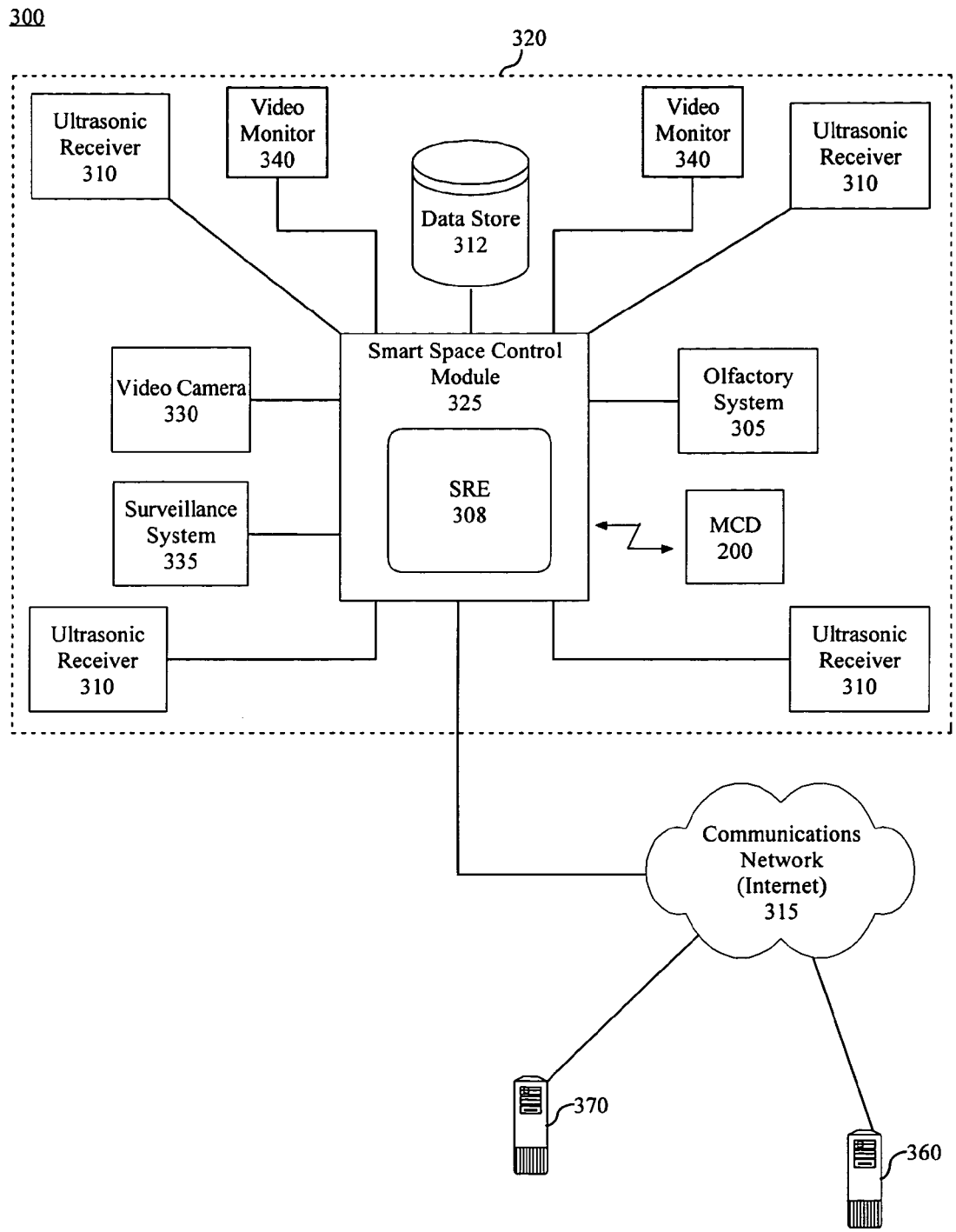
FIG. 3 is a schematic diagram illustrating a system within which an MCD can be utilized in accordance with another embodiment of the present invention.

FIG. 3 is a schematic diagram illustrating a system 300 within which a mobile communication device (MCD) 200 can be utilized in accordance with another embodiment of the present invention. It should be appreciated that the MCD 200 can be configured to operate in a variety of environments, including indoor and outdoor environments. FIG. 3 depicts a smart space 320, which can be a customized environment equipped with suitable transceivers, communications equipment, and other controller units. For example, a home can be so configured. Alternately, a workspace, caretaking facility, building, park, mall, and/or other space that can be occupied and/or inhabited by persons can be configured as a smart space. In one embodiment the MCD 200 can interact within smart space 320. In another embodiment, the MCD 200 can operate within a standard environment that has not been specifically modified for the needs of a physically and/or mentally challenged person or other MCD 200 user.

The MCD 200 can communicate with a smart space control module (SSCM) 325. The SSCM 325 can include a server disposed within a computing device, such as a personal computer, a laptop, or other information processing appliance that can be communicatively linked to the MCD 200. The MCD 200 can also communicate, via the SSCM 325, with components shown as being linked to the SSCM 325, such as at least one of a video camera 330, at least one of a ultrasonic receiver 310, a surveillance system 335, an olfactory system 305, or the like.

The MCD 200 can include one or more application programs that allow the user to access the functionality of the various systems and/or devices connected to the SSCM 325. In one embodiment, the MCD 200 can include a thin client and the SSCM 325 can function as an application server. The SSCM 325 can also be configured such that information exchanged between the MCD 200 and the SSCM 325 can be tailored for the needs, capabilities, and privileges of different users and/or MCDs.

It should be appreciated that the MCD 200 can communicate with the SSCM 325 using any of a variety of different communications mechanisms and that the MCD 200 is not limited to any specific communication mechanism. For example, the MCD 200 can initiate mobile telephone and/or conventional telephone calls to the SSCM 325 when the MCD 200 is not located within or proximate to the home within which the SSCM 325 is disposed. In another example, the MCD 200 can communicate with the SSCM 325 using short-range wireless communications when in range. In still another example, the MCD 200 can be linked to the SSCM 325 via one or more interface ports, or via the Internet.

In one aspect of the present invention, the location of the MCD 200 can be determined by the system 300. As shown, the ultrasonic receivers 310, which can be dispersed throughout a room or building, can detect a beacon signal emitted from the ultrasonic beacon disposed within the MCD 200. Information collected by the ultrasonic transceivers 310 can be provided to the SSCM 325 for processing such that the SSCM 325 can determine the location of the MCD 200 within the smart space. In another embodiment, a user can wear a jacket, vest, or other piece of clothing outfitted with one or more such beacons, for example on each shoulder. Such an arrangement allows the SSCM 325 to detect not only the location of a user, but also the orientation of the user. The position of the beacon(s), whether within the MCD 200 or a piece of clothing, can be calculated based upon the time required by the ultrasonic waves to reach each receiver. A trilateration technique also can be used.

Still, as noted, any of a variety of location detection mechanisms can be used. For example, digital image processing using one or more video cameras 330, sound, and/or motion detection technology, for example from the surveillance system 335, can be used to determine the location of a user. In the case where GPS or other satellite technology is used, the MCD 200 can determine its own location. Accordingly, such information can be sent to the SSCM 325 through any of the aforementioned communication techniques.

The MCD 200 can be configured to emit a combination of sensory indicators in an increasing order of intervention and activity in order to capture the attention of the user. Such sensory indicators can include text, audio, vibratory, or the like. It should be appreciated by those skilled in the art that the device is not limited to the sensory indicators described herein, and that the MCD can emit sensory indicators common to mobile commuting devices, such as PDAs, mobile phones, pagers, and the like.

The SSCM 325 can also be communicatively linked to sensory indicating devices, such as olfactory system 305. Olfactory system 305, which can include a microprocessor chip, circuitry, chemical-based system, or other apparatus, can be configured to emit a particular scent familiar to the user in order to capture the user's attention, or remind the user to perform a task. For example, the olfactory system 305 can emit the smell of coffee to remind the user that it is time to eat a meal. It should be appreciated by those skilled in the art that the SSCM 325 is not limited to the sensory indicators described herein, and that the SSCM 325 can be communicatively linked to other sensory indicator devices, such as flashing lights, audio speakers, or the like.

Using the location detection mechanisms described herein, the SSCM 325 can determine the location of the MCD 200, and therefore the user since the MCD 200 is designed to be on or close to the body of the user. Further, the SSCM 325 can be configured to determine which one of a plurality of video monitors 340 disposed within the smart space 320 is located most proximate to the MCD 200. Accordingly, the SSCM 325 can transmit a video clip to be presented on the selected video monitor 340 to be viewed by the user. The video clip can be configured to remind a user of a task the user needs to perform. Alternatively, the video clip can specify step by step instructions to perform a specific task.

In another aspect of the present invention, the SSCM 325 can be configured to execute a Speech Recognition Engine (SRE) 308. SRE 308 can be a software application executing within the SSCM 325. In one embodiment, a spoken utterance can be received within the MCD 200. For instance, a user may request assistance locating an item integral to performing a task, such as a medicine bottle, a pet, a remote control for a TV, or the like. Alternatively, a user may respond to an acknowledgement request from the system via a spoken utterance. Accordingly, the MCD 200 can be configured to send the spoken utterance to the SSCM 325 for analysis via the SRE 308. The spoken utterance can be converted to text and parsed to locate words which indicate that the user requires assistance, such as the words "HELP", or "YES". It should be appreciated that the user can also request assistance by activating controls on the MCD 200, such as buttons.

System 300 can also include a communications network 315 which can be communicatively linked to the MCD 200, for example via a mobile communications link, and the SSCM 325, as well as an external server 360, and a proxy server 370. In another embodiment of the present invention, the MCD 200 can include a thin client that is communicatively linked to a remotely located application server, such as external server 360. The proxy server 370 can be an intermediary between the MCD 200 and the external server 360 for providing security, administrative control, and other related functions for the MCD 200.

As depicted in FIG. 3, the SSCM 325 can include a data store 312. According to one embodiment of the present invention, the SSCM 325 can store within the data store 312 vital system information, such as historical data regarding user activities. The SSCM 325 can access the data store 312 to obtain information necessary to evaluate the effectiveness of the MCD 200, such as patient interaction. Data to be stored can include, for example, information regarding weekly home nurse visits, the user's daily schedule, and times when a pet is to be walked. Other vital data can include information regarding the user's medications, such as times, dosages, and types of medications to be ingested. Notably, while the data store 312 is depicted as being separate from the SSCM 325, it should be appreciated that the data store 312 also can be included within the SSCM 325.

Figure 4:
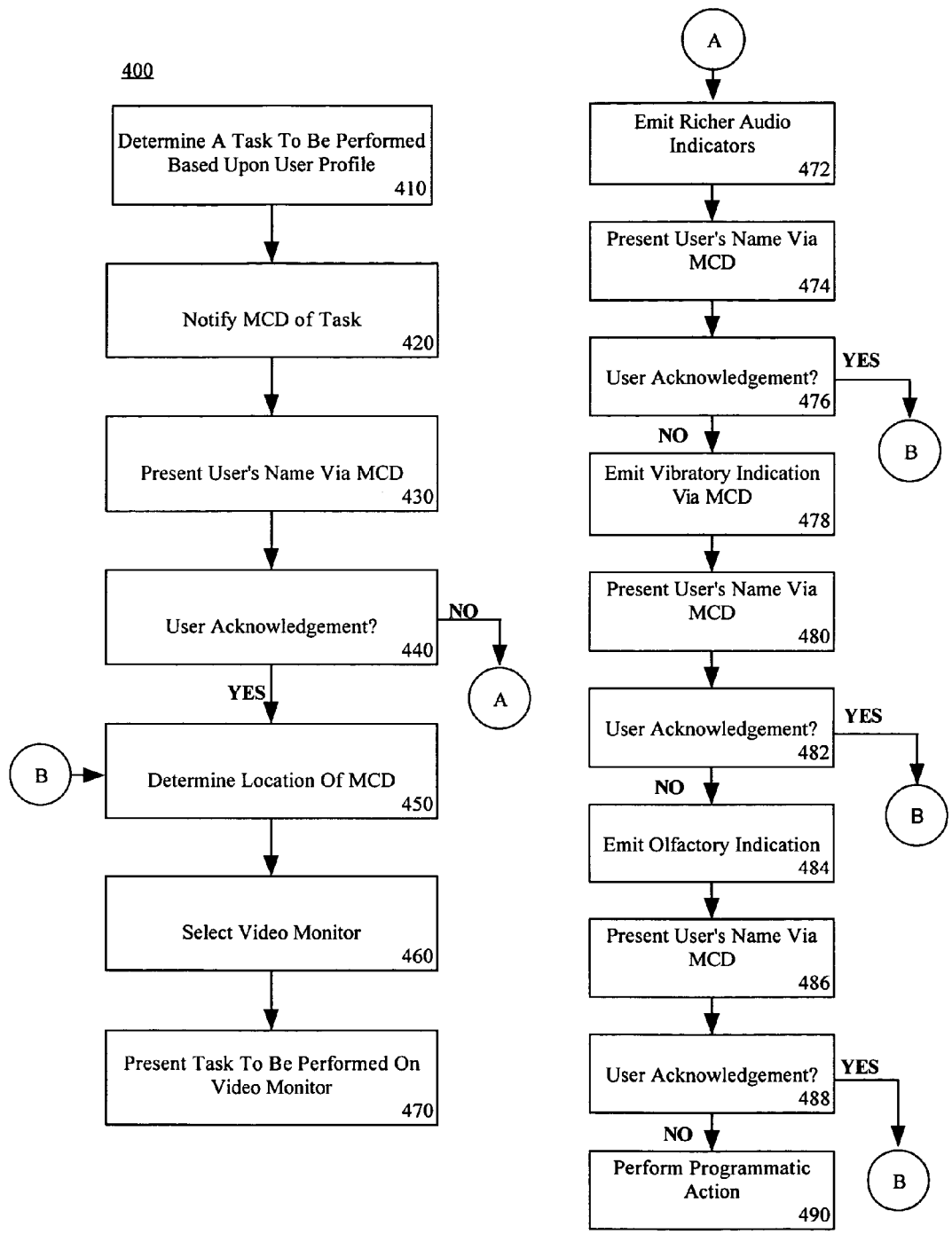
FIG. 4 is a flow chart illustrating a method in accordance with one embodiment of the present invention.

FIG. 4 is a flow chart illustrating a method 400 in accordance with one embodiment of the present invention. The method 400 can be used to capture the attention of the user by emitting a series of sensory indicators, via the MCD, in an increasing order of intervention and interactivity. Once the attention of the user has been successfully captured, the method can remind the user of a critical task using a video monitor. If the user fails to acknowledge the sensory indicators, a third party, such as a relative or caregiver, can be alerted.

The method can begin in step 410 by determining that the user is scheduled to perform a specific task, for example by the SSCM accessing the user's profile. In step 420, the MCD can be notified by the SSCM that the user needs to be reminded to perform the task. In step 430, the MCD can attempt to capture the user's attention by presenting the user's name through the MCD. It should be appreciated by one skilled in the art that the user's name can be presented on the MCD in a variety of ways, such as by playing an audio representation of the user's name or displaying a visual representation of the user's name.

In step 440, the MCD can be configured to prompt the user to acknowledge the presentation of the user's name. The user can acknowledge the presentation of the user's name using a control on the MCD, such as a button, or via a spoken acknowledgement. If the user has acknowledged the presentation of the user's name, the method can proceed to step 450. If not, the method can continue to step 472.

In step 450, the location of the MCD can be automatically determined using any of the location detection mechanisms described herein. In step 460, once the location of the MCD has been determined, the SSCM can select one of a plurality of video monitors disposed throughout the smart space. That is, the SSCM can select the video monitor which is most proximate to the MCD, and therefore the user. Accordingly, in step 470, the SSCM can remind the user to perform the scheduled task by activating a video clip on the video monitor.

Continuing with step 472, in the case where the user has failed to acknowledge the presentation of the user's name in step 440, the system can continue attempting to capture the user's attention by emitting a sequence of sensory indicators in an increasing order of intervention and interactivity. In step 472, the MCD can be configured to emit richer audio indicators, such as playing special songs, sounds, or increasing the volume of audio notifications. In step 474, the MCD can be configured to repeat the presentation of the user's name. In step 476, if the user has acknowledged the presentation of the user's name, the system can loop to step 450.

If, however, an acknowledgement has not been received, the system can proceed to step 478, where the MCD can be configured to emit a vibratory indication. The MCD can be configured to vibrate in order to capture the user's attention. In step 480, the MCD can once again repeat the presentation of the user's name. In step 482, if the user has acknowledged the presentation of the user's name, the system can loop to step 450. If, however, an acknowledgement has not been received, the system can proceed to step 484.

In step 484, the SSCM can be configured to send a request to the olfactory system to emit an olfactory indicator in order to capture the attention of the user. For example, in response to the request from the SSCM, the olfactory system can emit a scent which is familiar to the user, such as the odor of certain foods, beverages, flowers, or the like. In one embodiment of the present invention, the olfactory indicator can be reminiscent of a task routinely performed by the user, or of which the system is trying to remind the user. In step 486, the MCD can be configured to repeat the presentation of the user's name.

In step 488, if the user has acknowledged the presentation of the user's name, the system can loop to step 450. If not, the method can proceed to step 490 to take appropriate programmatic action, such as alerting a remote agent that the user is not responding to the sensory indicators. It should be appreciated by those skilled in the art that a remote agent can be alerted via e-mail, voice mail, text messaging, or the like.

The method 400 illustrates one embodiment of the present invention. It should be appreciated that other embodiments are contemplated. As such, the steps described with reference to method 400 are not to be construed as limiting. For example, the various sensory indicators described can be provided in varying order and repeated any number of times as may be appropriate to remind an individual, particularly one with mental and/or physical limitations.

Figure 5:
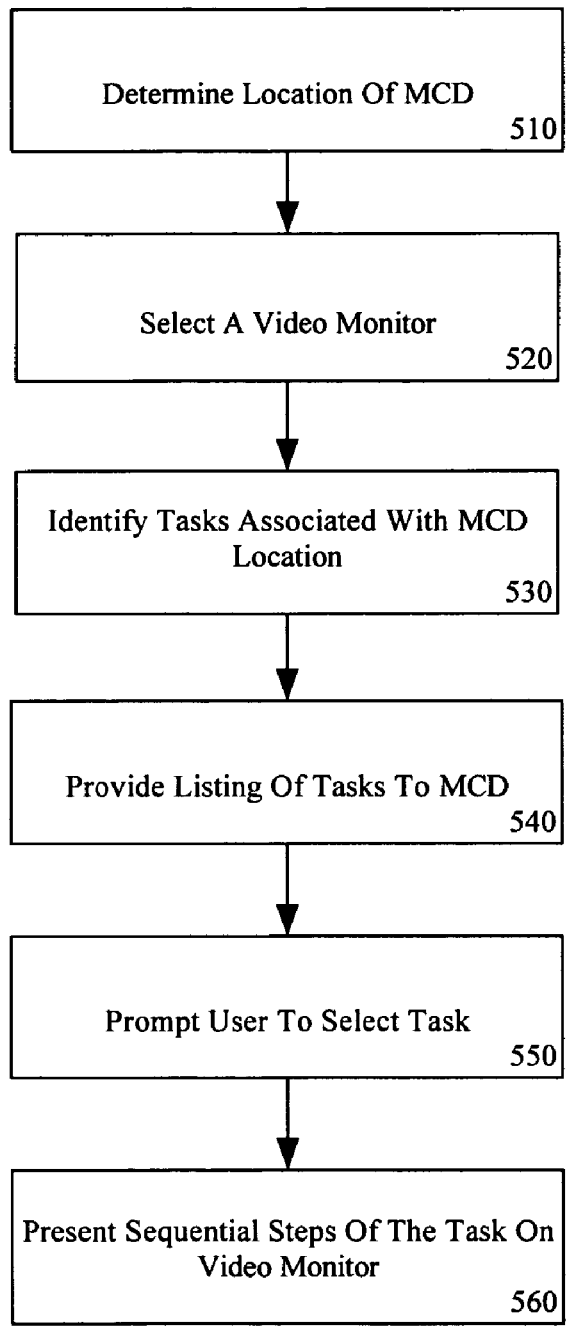
FIG. 5 is a flow chart illustrating a method in accordance with another embodiment of the present invention.

FIG. 5 is a flow chart illustrating a method 500 in accordance with another embodiment of the present invention. The method 500 can be used to provide step by step task instructions on a video monitor based upon the location of the MCD, and user interaction. In step 510, the location of the MCD can be determined. In step 520, the SSCM can select one of a plurality of video monitors disposed throughout the smart space. That is, the SSCM can select the video monitor which is most proximate to the MCD, and therefore the user.

In step 530, the SSCM can identify one or more tasks associated with the present location of the MCD determined in step 510. For example, if the SSCM has detected that the user has entered the kitchen, the SSCM can identify tasks that the user might want to perform while in the kitchen, such as preparing a meal, feeding a pet, drinking a glass of water, taking medication, and the like. It should be appreciated by those skilled in the art, however, that while tasks can be categorized according to location, they can also be cross-referenced according to the user's schedule. That is, the SSCM can remind the user to perform a scheduled task regardless of the user's location. For example, when the user enters the kitchen, the SSCM can first query the user's profile to see whether it is time for the user to perform a specific kitchen task. If the user's profile indicates instead that it is time for the user to perform a non-kitchen task, such as bathing, the SSCM can remind the user to take a shower even if though the user is in the kitchen. Accordingly, the SSCM can track the user's schedule in accordance with the user's stored profile.

In step 540, the SSCM can send the listing of tasks associated with the user's location to the MCD for presentation. In step 550, the user can be prompted to select a task from the list. It should be appreciated by those skilled in the art that the user can select a task using a control on the MCD, such as a button, or via spoken verification. In step 560, the SSCM can activate a video clip on the video monitor depicting step by step instructions on how to perform the task selected by the user.

While the method 500 illustrates the case where the user is prompted to select a particular task, directions also can be provided to the user in an automatic fashion in accordance with the user's store profile. For example, at a designated time, indicated by the user's profile, the user can be reminded to perform a task such as taking medication. In that case, the system automatically can locate the user and being prompting and/or providing video instruction to the user via a monitor proximate to the user.

Figure 6:
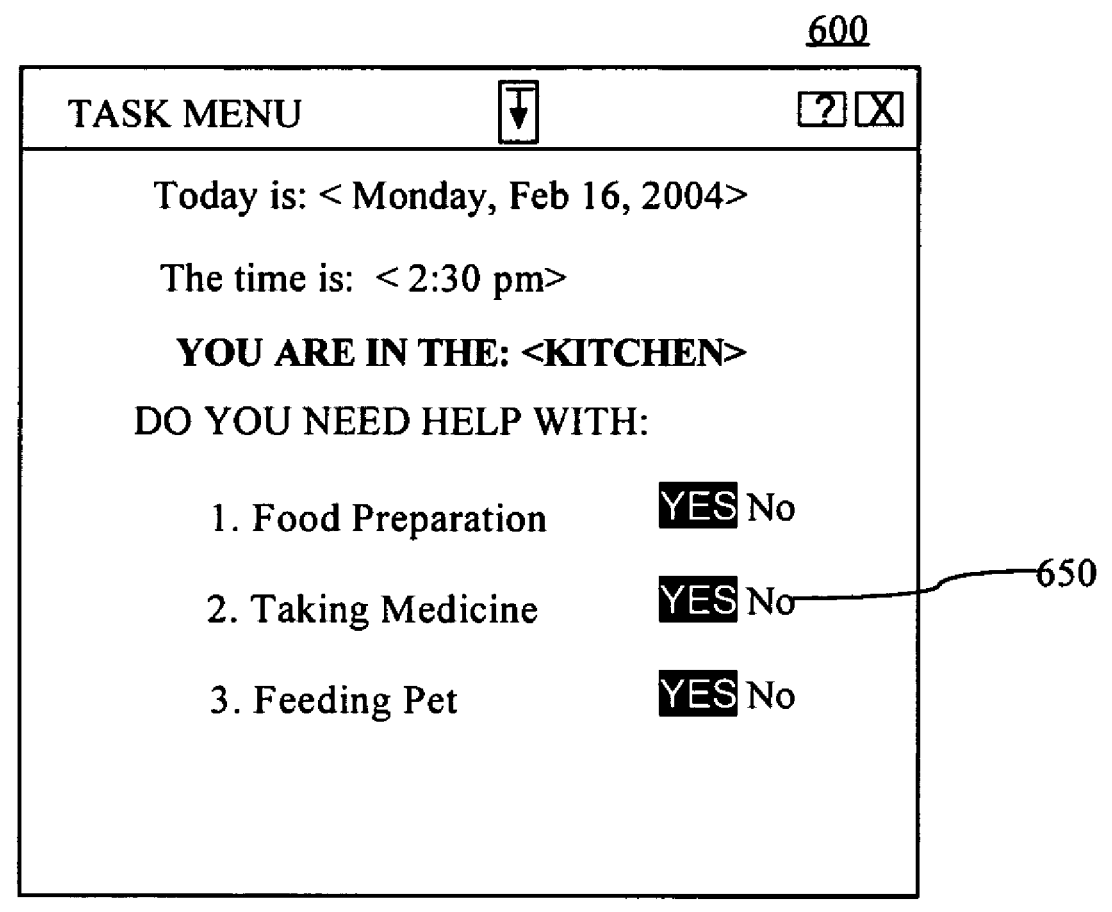

FIG. 6 is a schematic diagram illustrating one embodiment of a graphical user interface (GUI) 600 for use with the MCD. As described herein, the SSCM can determine a list of tasks typically associated with a location within the smart space. The GUI 600 can be presented to the user when the SSMC detects that the MCD has arrived at a specific location. The GUI 600 depicts an example of a "task menu" which can allow a user to initiate a request for step by step instruction of a particular task typically performed in the location, such as a kitchen. The MCD can be configured to open a dialog box 650 to present the list of tasks associated with the location. Activation of a "YES" selection by the user can cause another GUI (not shown) to be presented to the user which is dedicated to the selected task. For example, in the case where the user selects the option "food preparation", the MCD can display a screen indicating a variety of food choices or meals to choose from.

GUI 600 has been provided for purposes of illustration only. It should be appreciated by those skilled in the art that a GUI can be implemented in a variety of different configurations using an assortment of control mechanisms. As such, GUI 600 is not intended as a limitation of the present invention. Notably, GUI 600 depicts the user being presented with data in a text format. It should also be appreciated, however, that a user can be presented with task information in a audible format.

The present invention can be realized in hardware, software, or a combination of hardware and software. The present invention can be realized in a centralized fashion in one computer system or in a distributed fashion where different elements are spread across several interconnected computer systems. Any kind of computer system or other apparatus adapted for carrying out the methods described herein is suited. A typical combination of hardware and software can be a general-purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention.

What is claimed is:

1. A method of task and memory assistance using a mobile communication device, the method comprising the steps of:
    storing a profile of a user;
    determining a task based on the user profile;
    notifying the mobile communication device of the task; and
    providing sensory indicators for a predetermined number of notifications in an increasing order of intervention until an acknowledgement is received from the user, and if after the predetermined number of notifications acknowledgement has not been received from the user, notifying a designated third party that no acknowledgement is detected from the user, wherein providing sensory indicators in an increasing order of intervention includes at last one of playing a predetermined song or sounds at a volume that iteratively increases with each subsequent providing of the sensory indicator and emitting a vibratory indicator that iteratively increases in intensity with each subsequent providing of the sensory indicator.

2. The method of claim 1, said notifying step comprising notifying the mobile communication device over a short range wireless network.

3. The method of claim 1, said providing step further comprising:
    emitting audio indicators from the mobile communication device;
    emitting vibratory indicators from the mobile communication device; and
    emitting an olfactory indicator from an olfactory system.

4. The method of claim 1, further comprising determining a location of the mobile communication device.

5. The method of claim 4, further comprising:
    selecting one of a plurality of monitors disposed throughout a defined space according to the location, wherein the selected monitor is most proximate to the mobile communication device; and
    presenting on the selected monitor information pertaining to the task.

6. A method for providing task instruction using a mobile communication device comprising the steps of:
    storing a profile of user tasks, wherein each task is associated with a location within a defined space;
    determining a location of the mobile communication device within the defined space;
    identifying one or more tasks associated with the location;
    providing a listing of one or more of the tasks associated with the location to the user via the mobile communication device ; and
    notifying the user that the one or more tasks are to be performed, the notifying including providing sensory indicators in an increasing order of intervention until an acknowledgement is received from the user, wherein providing sensory indicators in an increasing order of intervention includes at least one of playing a predetermined song or sounds familiar to the user at a volume that iteratively increases with each subsequent providing of the sensory indicator and emitting a vibratory indicator that iteratively increases in intensity with each subsequent providing of the sensory indicator.

7. The method of claim 6, further comprising:
    selecting one of a plurality of video monitors disposed throughout the defined space according to the location, wherein the selected monitor is most proximate to the mobile communication device; and
    presenting on the selected monitor information pertaining to a task selected by the user.

8. The method of claim 6, wherein the step of determining a location comprises detecting with a plurality of ultrasonic receivers an ultrasonic signal emitted by an ultrasonic transponder connected to the mobile communication device.

9. A system for providing memory assistance, comprising:
    a location determining mechanism;
    a mobile communication device configured to interact with the location tracking mechanism;
    a server in communication with the location tracking mechanism and the mobile communication device, wherein the server is local to the mobile communication device, said server having a listing of tasks;
    a plurality of monitors, wherein said server selects one of the plurality of monitors most proximate to the user based upon information from the location tracking mechanism and causes information corresponding to one of the tasks to be presented upon the selected monitor; and
    notifying the user that the one or more tasks are to be performed, the notifying including providing sensory indicators in an increasing order of intervention until an acknowledgement is received from the user, wherein providing sensory indicators in an increasing order of intervention includes at last one of playing a predetermined song or sounds at a volume that iteratively increases with each subsequent providing of the sensory indicator and emitting a vibratory indicator that iteratively increases in intensity with each subsequent providing of the sensory indicator.

10. The system of claim 9, wherein the server delivers video pertaining one of the tasks to the selected monitor.

11. The system of claim 9, wherein the location determining mechanism comprises a plurality of ultrasonic receivers for detecting an ultrasonic signal emitted by an ultrasonic transponder connected to the mobile communication device.

12. A machine readable storage, having stored thereon a computer program having a plurality of code sections executable by a machine for causing the machine to perform the steps of:
    storing a profile of a user;
    determining a task based on the user profile;
    notifying the mobile communication device of the task; and providing sensory indicators for a predetermined number of notifications in an increasing order of intervention until an acknowledgement is received from the user, and if after the predetermined number of notifications acknowledgement has not been received from the user, notifying a designated third party that no acknowledgement is detected from the user, wherein providing sensory indicators in an increasing order of intervention includes at least one of playing a predetermined song or sounds familiar to the user at a volume that iteratively increases with each subsequent providing of the sensory indicator and emitting a vibratory indicator that iteratively increases in intensity with each subsequent providing of the sensory indicator.

13. The machine readable storage of claim 12, said notifying step comprising notifying the mobile communication device over a short range wireless network.

14. The machine readable storage of claim 12, said providing step further comprising:
   emitting audio indicators from a mobile communication device;
   emitting vibratory indicators from a mobile communication device; and
   emitting an olfactory indicator from an olfactory system.

15. The machine readable storage of claim 12, further comprising determining a location of the mobile communication device.

16. The machine readable storage of claim 15, further comprising:
   selecting one of a plurality of monitors disposed throughout a defined space according to the location, wherein the selected monitor is most proximate to the mobile communication device; and
   presenting on the selected monitor information pertaining to the task.

17. A machine readable storage, having stored thereon a computer program having a plurality of code sections executable by a machine for causing the machine to perform the steps of:
   storing a profile of user tasks, wherein each task is associated with a location within a defined space;
   determining the location of the mobile communication device within the defined space;
   identifying one or more tasks associated with the location;
   providing a listing of the one or more tasks associated with the location to the user via the mobile communication device;
   notifying the user that the one or more tasks are to be performed, the notifying including providing sensory indicators in an increasing order of intervention until an acknowledgement is received from the user, wherein providing sensory indicators in an increasing order of intervention includes at least one of playing a predetermined song or sounds familiar to the user at a volume that iteratively increases with each subsequent providing of the sensory indicator and emitting a vibratory indicator that iteratively increases in intensity with each subsequent providing of the sensory indicator.

18. The machine readable storage of claim 17, further comprising:
   selecting one of a plurality of video monitors disposed throughout the defined space according to the location, wherein the selected monitor is most proximate to the mobile communication device; and
   presenting on the selected monitor information pertaining to a task selected by the user.

* * * * *